(12) United States Patent
Hong et al.

(10) Patent No.: US 11,484,834 B2
(45) Date of Patent: Nov. 1, 2022

(54) METHOD FOR REDUCING NITROGEN DIOXIDE IN EXHAUST GAS GENERATED DURING OLEFIN PRODUCTION PROCESS

(71) Applicants: SK GAS CO., LTD., Gyeonggi-do (KR); KOCAT INC., Gyeonggi-do (KR)

(72) Inventors: Ung Gi Hong, Gyeonggi-do (KR); Mi Young Lee, Seoul (KR); Deuk Soo Park, Gyeonggi-do (KR); Jung Ho Kim, Seoul (KR); Jin Young Kim, Gyeonggi-do (KR); Chang Hee Yang, Gyeonggi-do (KR)

(73) Assignees: SK Gas Co., Ltd., Gyeonggi-do (KR); Kocat Inc., Gyeonggi-do (KR)

( * ) Notice: Subject to any disclaimer, the term of this patent is extended or adjusted under 35 U.S.C. 154(b) by 185 days.

(21) Appl. No.: 17/050,877

(22) PCT Filed: Jun. 4, 2018

(86) PCT No.: PCT/KR2018/006337
§ 371 (c)(1),
(2) Date: Jul. 21, 2021

(87) PCT Pub. No.: WO2019/216475
PCT Pub. Date: Nov. 14, 2019

(65) Prior Publication Data
US 2021/0387142 A1    Dec. 16, 2021

(30) Foreign Application Priority Data

May 8, 2018  (KR) .......................... 10-2018-0052654

(51) Int. Cl.
*B01D 53/56*  (2006.01)
*B01D 53/79*  (2006.01)

(52) U.S. Cl.
CPC ............. *B01D 53/79* (2013.01); *B01D 53/56* (2013.01); *B01D 2251/21* (2013.01); *B01D 2257/402* (2013.01)

(58) Field of Classification Search
CPC .. B01D 53/79; B01D 53/56; B01D 2257/402; B01D 2251/21; Y02A 50/20; Y02C 20/10; C07C 5/333; C07C 11/06
See application file for complete search history.

(56) References Cited

U.S. PATENT DOCUMENTS 5,547,650 A * 8/1996 Edgar .................... B01D 53/56
                                                    423/235
6,495,108 B1 * 12/2002 Rising ................... B01D 53/56
                                                    422/186

(Continued)

FOREIGN PATENT DOCUMENTS

KR    1999-0069935 A       9/1999
KR    2012 0 092744 A  *   8/2012  ............ B01D 47/06

(Continued)

*Primary Examiner* — Timothy C Vanoy
(74) *Attorney, Agent, or Firm* — Fay Sharpe LLP (57) ABSTRACT

Provided is a method for using selective non-catalytic reduction to reduce nitrogen dioxide in exhaust gas generated during an olefin production process. Nitrogen dioxide generated in a catalyst regeneration step of a continuous PDH process can be efficiently removed by the method of the present disclosure. Ultimately, the generation of visible fumes can be prevented through the removal of nitrogen dioxide.

5 Claims, 5 Drawing Sheets

(56) References Cited

U.S. PATENT DOCUMENTS

2007/0130823 A1    6/2007   Appleby et al.
2011/0085955 A1 *  4/2011   Larsson ............. B01D 53/8625
                                                                         423/230

FOREIGN PATENT DOCUMENTS

| KR | 10 1 199 267 B1 * | 11/2012 | ............. B01D 53/78 |
| KR | 10-1199265 B | 11/2012 | |
| KR | 10-1199267 B | 11/2012 | |
| KR | 10-2014-0027854 A | 3/2014 | |
| KR | 10-1758226 B | 1/2017 | |
| KR | 10-2017-0071793 A | 6/2017 | |
| RU | 2 709 811 C1 * | 12/2019 | ............. B01J 23/10 |
| TW | 2004 003 218 A * | 3/2004 | ............. C10G 11/00 |
| WO | WO 1988/006487 | 9/1988 | |
| WO | WO 2007 142 496 A1 * | 12/2007 | ........... B01D 47/063 |

\* cited by examiner

Performance depending on EtOH temperature & molar ratio

Performance depending on EG temperature & molar ratio

FIG. 4

EtOH:EG=40:60 Performance measurement

EtOH:EG=60:40 Performance measurement

METHOD FOR REDUCING NITROGEN DIOXIDE IN EXHAUST GAS GENERATED DURING OLEFIN PRODUCTION PROCESS

This application is a 371 of PCT Application No. PCT/KR2018/006337 filed Jun. 4, 2018, which claims priority to Korean Patent Application No. 10-2018-0052654 filed May 8, 2018, the contents of which are entirely incorporated herein by reference.

TECHNICAL FIELD

The present disclosure relates to a method of decreasing nitrogen dioxide content in exhaust gas generated during an olefin production process, and more particularly to a method of decreasing nitrogen dioxide content in exhaust gas before discharging exhaust gas, generated in the course of regeneration of a catalyst used for a propane dehydrogenation (PDH) process, into the atmosphere.

BACKGROUND ART

Olefins such as ethylene and propylene are widely used in the petrochemical industry. Typically, these olefins are obtained through thermal cracking of naphtha. However, in the petrochemical industry, larger amounts of olefins are required, and in order to satisfy this demand, an olefin production method using a process of dehydrogenation of lower hydrocarbons such as ethane and propane in the presence of a catalyst has been developed. In this regard, KR 10-1758226 discloses a catalyst for preparing an olefin through dehydrogenation of a hydrocarbon.

The catalyst used in the dehydrogenation process may be regenerated through reaction with air. However, exhaust gas containing nitrogen dioxide is generated in the catalyst regeneration step at a high temperature, which is undesirable. The exhaust gas discharged from the catalyst regeneration step is discharged into the atmosphere through a stack. In general, nitrogen oxide ($NO_x$) contained in exhaust gas includes nitrogen monoxide, nitrogen dioxide, and nitrous oxide, and is a representative substance that causes environmental pollution. Exhaust gas controlled to the level that the nitrogen oxide content in exhaust gas satisfies emission limits in accordance with recent stringent environmental standards is discharged into the atmosphere by changing processing conditions. However, even when the nitrogen oxide content in exhaust gas meets the emission limit, if the concentration of nitrogen dioxide in exhaust gas exceeds about 15 ppm, a yellow plume may occur. Such a yellow plume causes serious psychological and visible impacts on nearby residents and needs to be eliminated. In order to prevent the generation of yellow plumes, a technique capable of decreasing nitrogen dioxide content in exhaust gas is required.

In order to decrease nitrogen dioxide content in exhaust gas in the related art, research into combustion control and exhaust gas treatment technology in the fields of power plants or internal combustion engines has been continuously conducted. Techniques for decreasing nitrogen oxide content through exhaust gas treatment are largely classified into two types: selective catalytic reduction (SCR) using a catalyst and selective non-catalytic reduction (SNCR) not using a catalyst.

SCR is effective at removing nitrogen dioxide, but requires an increase in the size of a facility in order to install a catalyst apparatus, and thus there occur problems in which a high investment cost is required in order to eliminate even a small yellow plume caused by nitrogen dioxide and the installation area increases due to the catalyst apparatus installation, so additional land has to be obtained for the facility expansion. A method of decreasing the generation of yellow plumes using SCR is disclosed in KR 1999-0069935.

On the other hand, SNCR is low in efficiency of decreasing nitrogen dioxide content compared to SCR, but the installation cost and period are short and a large additional facility is not required, and thus the nitrogen dioxide content generated during processing may be more effectively decreased. A method of decreasing the generation of yellow plumes using SNCR is disclosed in KR 10-1199265. However, the above related patents merely disclose nitrogen dioxide removal technology for application to power plants and internal combustion engines, but do not disclose nitrogen dioxide removal technology suitable for use in the PDH process.

It is not appropriate to directly apply the above related techniques for decreasing the nitrogen dioxide content generated during the operation of power plants in order to decrease the nitrogen dioxide content generated in an olefin production process. This is because the composition of exhaust gas generated in a power plant is different from the composition of exhaust gas generated in a PDH process, and more particularly because $NO_2$ content in exhaust gas is much higher due to the catalytic reaction in exhaust gas generated in the PDH process than in typical exhaust gas generated in a power plant. Moreover, the technique for decreasing nitrogen dioxide content is applied for a short period of time at medium and low loads in power plants, but must be applied all the time in the PDH process, in which a reaction is continuously carried out for 24 hr. Accordingly, it is necessary to develop a technique for decreasing nitrogen dioxide content suitable for the PDH process, separately from the technique for decreasing nitrogen dioxide content that is applied to conventional power plants and internal combustion engines.

In particular, only the technique of removing nitrogen dioxide using SCR in the PDH process is commercialized at present, and the use of SNCR in the PDH process has not yet been realized. Upon SCR in a continuously operating PDH process, the lifetime of the catalyst is short compared to intermittent use thereof in power plants. Furthermore, the case in which the operation of the process is stopped in order to replace the catalyst is problematic in that the processing loss is enormous. Accordingly, the technique for decreasing nitrogen dioxide content using SNCR in the PDH process is becoming more and more important.

DISCLOSURE

Technical Problem

Therefore, an aspect of the present disclosure is to provide a method of decreasing nitrogen dioxide content in exhaust gas using SNCR, suitable for application to exhaust gas generated in an olefin production process using a dehydrogenation reaction.

Technical Solution

In order to accomplish the above aspect, the present disclosure provides a method of decreasing nitrogen dioxide content in exhaust gas generated during an olefin production process using selective non-catalytic reduction, comprising: (a) providing exhaust gas containing nitrogen dioxide generated in an olefin production process; (b) reducing nitrogen dioxide by injecting a mixed reducing agent to the exhaust gas, the mixed reducing agent comprising glycerin and ethylene glycol; and (c) discharging the exhaust gas subjected to step (b) into the atmosphere.

In an embodiment of the present disclosure, the nitrogen dioxide content in the exhaust gas that is provided may be 20 ppm or more.

In an embodiment of the present disclosure, the oxygen content in the exhaust gas that is provided may be 16 to 20 mol %.

In an embodiment of the present disclosure, the hydrocarbon content in the exhaust gas that is provided may be 50 to 2000 ppmv.

In an embodiment of the present disclosure, the temperature of the exhaust gas that is provided may be 500 to 600° C.

In an embodiment of the present disclosure, step (b) may be performed in a waste heat boiler (WHB).

In an embodiment of the present disclosure, the mixed reducing agent may be injected at the position of a waste heat boiler at which the temperature of the exhaust gas is 350 to 450° C.

In an embodiment of the present disclosure, the mixed reducing agent may be injected such that the molar ratio of the mixed reducing agent/nitrogen dioxide is 0.5-4.

In an embodiment of the present disclosure, the molar ratio of glycerin to ethylene glycol in the mixed reducing agent may be 55-80: 20-45.

In an embodiment of the present disclosure, the nitrogen dioxide content in the exhaust gas that is discharged in step (c) may be 12 ppm or less.

Advantageous Effects

According to the present disclosure, a method of removing nitrogen dioxide is capable of efficiently removing nitrogen dioxide generated in a catalyst regeneration step in a PDH process that operates continuously. Thus, it is possible to prevent the generation of yellow plumes by decreasing the nitrogen dioxide content in exhaust gas to less than 15 ppm.

In addition, according to the present disclosure, the method of removing nitrogen dioxide can be performed at the same time as heat exchange between exhaust gas and water in a waste heat boiler, and thus an additional reactor is obviated and there is no need to exchange an aged catalyst due to the absence of a catalyst, so economical benefits can occur from the viewpoints of installation and maintenance costs.

BEST MODE

The objectives, specific advantages and novel features of the present disclosure will become more apparent from the following detailed description and preferred embodiments associated with the accompanying drawings, but the present disclosure is not necessarily limited thereto. Furthermore, in the description of the present disclosure, it is to be noted that when a detailed description of known techniques related with the present disclosure may make the gist of the present disclosure unclear, such description will be omitted.

In the present disclosure, the expressions "decreasing nitrogen dioxide content", "removing nitrogen dioxide" and "reducing nitrogen dioxide" refer to lowering the amount of nitrogen dioxide in exhaust gas, and have the same meaning, and the above expressions may be used interchangeably in the present disclosure.

Hereinafter, a detailed description will be given of the present disclosure with reference to the appended drawings.

The present disclosure pertains to a method of decreasing nitrogen dioxide content in exhaust gas through selective non-catalytic reduction. As the feed of the present disclosure, exhaust gas generated during an olefin production process is provided. Specifically, the exhaust gas may be generated during an olefin production process using a hydrocarbon dehydrogenation reaction. More specifically, the exhaust gas may be containing nitrogen dioxide generated in the step of regenerating a catalyst used in an olefin production process, particularly a PDH process.

Figure 1:
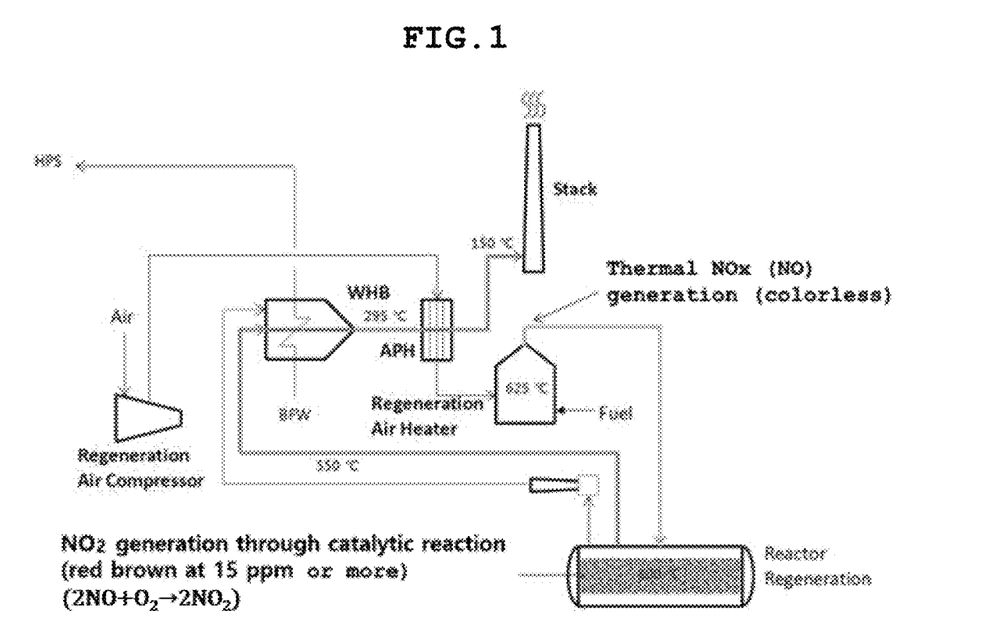
FIG. 1 is a schematic flowchart showing the discharge of exhaust gas containing nitrogen dioxide generated in a catalyst regeneration step during an olefin production process into the atmosphere.

FIG. 1 is a schematic flowchart showing the discharge of exhaust gas containing nitrogen dioxide generated in the catalyst regeneration step during the olefin production process into the atmosphere. With reference to FIG. 1, in order to regenerate the catalyst, air is compressed and heated through a compressor and heater and is then supplied to a catalyst regeneration reactor. The compressed and heated air includes nitrogen oxide ($NO_x$) due to oxidation of nitrogen in the air during heating. When the air is supplied to the catalyst regeneration reactor and the catalyst regeneration reaction proceeds, a conversion reaction of nitrogen and nitrogen monoxide into nitrogen dioxide in the reactor occurs as a side reaction. The gas of the catalyst regeneration reactor containing nitrogen dioxide generated after the reaction is discharged as exhaust gas, and is emitted into the atmosphere through a stack.

Nitrogen dioxide in the exhaust gas may generate a yellow plume when discharged into the atmosphere. Whether a yellow plume occurs depends on the concentration of nitrogen dioxide in the gas. In general, it is known that a yellow plume occurs when the exhaust gas contains 15 ppm or more of nitrogen dioxide therein. Thus, according to an embodiment of the present disclosure, the nitrogen dioxide content in the exhaust gas may be 15 ppm or more. For example, the nitrogen dioxide content in the exhaust gas may be 15 ppm or more, 20 ppm or more, 25 ppm or more, 30 ppm or more, 35 ppm or more, 40 ppm or more, 45 ppm or more, 50 ppm or more, or 55 ppm or more. According to another embodiment of the present disclosure, the nitrogen dioxide content in the exhaust gas may be 60 ppm or more.

Typically, the oxygen content in exhaust gas discharged from a power plant and the like is known to be about 12 mol %, and the exhaust gas generated during the olefin production process of the present disclosure has higher oxygen content. According to an embodiment of the present disclosure, the oxygen content in the exhaust gas may be 16 to 20 mol %. Specifically, the oxygen content in the exhaust gas may be 17 to 19 mol %, and particularly 17.5 to 19 mol %. Due to the difference in the oxygen content in the exhaust gas, an environment having a high oxygen concentration makes the conversion of nitrogen dioxide into nitrogen monoxide or nitrogen more difficult, and thus the process of decreasing nitrogen dioxide content according to the present disclosure requires processing conditions different from those used in conventional power plants and the like.

Moreover, about 80% of $NO_x$ in exhaust gas discharged from a conventional power plant and the like is nitrogen monoxide, whereas about 70% or more, particularly about 80% or more of $NO_x$ in exhaust gas generated during the olefin production process of the present disclosure is composed of nitrogen dioxide. The processing conditions used in conventional power plants and the like make it difficult to achieve the efficiency of decreasing nitrogen dioxide content as desired in the present disclosure, and therefore, processing conditions different from conventional processing conditions are required.

The catalyst regeneration reaction is carried out at a high temperature of about 600° C. or higher, and is an exothermic reaction, and thus exhaust gas discharged from the catalyst regeneration reactor may be a high-temperature gas at about 600° C. Therefore, according to an embodiment of the present disclosure, the temperature of the exhaust gas may be 500 to 600° C., preferably 550 to 600° C. The temperature of the exhaust gas provided as the feed of the present disclosure is high enough to perform a reduction reaction for decreasing nitrogen dioxide content when discharged from the catalyst regeneration reactor, thereby obviating an additional heating step.

Nitrogen dioxide in the exhaust gas is converted into nitrogen monoxide or nitrogen molecules through a reduction reaction. The reduction process of the present disclosure is performed using selective non-catalytic reduction, and does not use a catalyst that promotes a reduction reaction but uses only a reducing agent. As the reducing agent used to decrease nitrogen dioxide content in the present disclosure, a mixed reducing agent is used, and the mixed reducing agent comprises glycerin and ethylene glycol.

According to an embodiment of the present disclosure, reduction of nitrogen dioxide in the exhaust gas may be performed in a waste heat boiler (WHB). Meanwhile, the catalyst regeneration step in the olefin production process requires a large amount of air compared to other processes such as a naphtha-cracking process or power plants and the like, and thus the importance of an air compressor is very high. Accordingly, when ΔP increases between an upstream side and a downstream side of the air compressor, there is a problem of increased investment cost due to the compressor. Therefore, in order to minimize the ΔP, it may be possible to achieve the purpose of the present disclosure by installing a grid nozzle in a waste heat boiler to thus supply a reducing agent, without using a separate reduction device. Taking advantage of SNCR, the present disclosure makes it possible to achieve the goal of decreasing nitrogen dioxide content by injecting a reducing agent into a device typically included in an olefin production process, such as a WHB, without the need for a separate nitrogen dioxide removal reactor. Thus, economic benefits may occur from the viewpoints of installation and maintenance costs due to the additional device. Moreover, as described below, the reducing agent is preferably injected at a temperature suitable for the reduction reaction to be carried out. When a WHB is used, the temperature of the exhaust gas is lowered through heat exchange between exhaust gas and boiler feed water (BFW), thus facilitating injection of a reducing agent at a specific position in the WHB in which exhaust gas flows at a specific temperature. Furthermore, in the overall olefin production process, as illustrated in FIG. 1, high-pressure steam (HPS) is generated from BFW through heat exchange, thus conveying obvious economic benefits because the thermal energy of the exhaust gas is recycled.

According to an embodiment of the present disclosure, the reducing agent may be injected into the exhaust gas at the position of the WHB at which the temperature of the exhaust gas supplied to the WHB is 350 to 450° C. The injection temperature is preferably 370 to 420° C., and more preferably 390 to 410° C. The injection temperature affects the efficiency with which the nitrogen dioxide content in the exhaust gas is decreased. Particularly, if the injection temperature is lower than 350° C., the temperature is too low for the reduction reaction to occur, making it difficult to achieve the desired efficiency of decreasing nitrogen dioxide content. On the other hand, if the injection temperature exceeds 450° C., an oxidation reaction due to oxygen present in the exhaust gas may occur before the reduction reaction. For example, when the injection temperature of the reducing agent of the present disclosure is lower than 350° C. or higher than 450° C., there is a problem in which the efficiency of decreasing nitrogen dioxide content does not reach the level at which the generation of yellow plumes is prevented.

According to an embodiment of the present disclosure, the reducing agent may be injected such that the molar ratio of the reducing agent/nitrogen dioxide is 0.5-4. Here, the molar ratio is a value obtained by dividing the total molar amount of the mixed reducing agent by the total molar amount of nitrogen dioxide in exhaust gas. The molar ratio of the reducing agent/nitrogen dioxide is preferably 1-4, and more preferably 1.5-3.5. If the molar ratio thereof is less than 0.5, the amount of the reducing agent that is injected is much smaller than the amount of nitrogen dioxide in the exhaust gas, making it difficult to achieve the goal of decreasing nitrogen dioxide content. On the other hand, if the molar ratio thereof exceeds 4, a cost problem may occur due to an increase in the amount of the reducing agent that is consumed due to excessive injection, and also, nitrogen oxides or other byproducts may be generated due to side reactions of the reducing agent, which is injected in excess.

As described above, a mixed reducing agent is used to remove nitrogen dioxide generated in the olefin production process of the present disclosure, and the composition ratio of glycerin and ethylene glycol of the mixed reducing agent also affects the efficiency of decreasing nitrogen dioxide content. According to an embodiment of the present disclosure, the molar ratio of glycerin to ethylene glycol in the mixed reducing agent may be 55-80: 20-45. Preferably, the molar ratio thereof is 60-80: 20-40, and more preferably 60-70: 30-40. When the composition ratio of glycerin and ethylene glycol in the mixed reducing agent falls outside the above range, it is impossible to reach the desired efficiency of decreasing nitrogen dioxide content in the present disclosure. In particular, when glycerin is included in the mixed reducing agent in excess of the above molar ratio, the viscosity of the mixed reducing agent becomes extremely high, fluidity deteriorates, and the possibility of causing problems in a low-temperature environment such as during the winter increases.

Meanwhile, an additional reducing agent may be optionally injected at a position different from the position of injection of the mixed reducing agent in the WHB along with the injection of the mixed reducing agent as described above. The additional reducing agent may be injected upstream or downstream of the position of injection of the mixed reducing agent, and is preferably injected upstream of the mixed reducing agent. According to an embodiment of the present disclosure, the additional reducing agent may be injected into the exhaust gas at a position of the WHB at which the temperature of the exhaust gas supplied to the WHB is 550° C. or less but exceeds 450° C. The temperature at which the reducing agent is injected is preferably 470 to 520° C., and more preferably 490 to 510° C.

Also, the additional reducing agent is not particularly limited, so long as it is able to reduce nitrogen dioxide in exhaust gas, unlike the mixed reducing agent. For example, the additional reducing agent may include a hydrocarbon compound or a carbohydrate containing a reducing functional group such as a hydroxyl group, an ether group, an aldehyde group, a ketone group, etc. However, a reducing agent containing nitrogen may increase the amount of nitrogen oxide that is generated due to the reaction thereof with oxygen in the air, and is thus unsuitable as the additional reducing agent of the present disclosure.

As the additional reducing agent, examples of the hydrocarbon compound may include ethanol, isobutyl alcohol, isopropyl alcohol, glycerin, allyl alcohol, tert-butanol, n-propyl alcohol, ethylene glycol, methoxypropanol, n-butyl alcohol, n-octyl alcohol, isooctanol, 2-ethyl hexanol, acetyl acetonate, maleic acid, fumaric acid, glyoxal, glyoxalic acid, cyclohexanol, cyclohexanone, 1,3-propanediol, 1,2-propanediol, propanal, 1,4-butanediol, isobutyraldehyde, n-butyraldehyde, pentanediol, 1,5-hexanediol, glutaraldehyde, dioxane, trioxane, furan, tetrahydrofuran, tartaric acid, citric acid, diethyl acetaldehyde, propargyl alcohol, tert-butyl ether, glycerin carbonate, glyceraldehyde, glyceric acid, tetralol, tetralone, benzaldehyde, terephthaldehyde, 1,4-cyclohexanedialcohol, xylenol and isomers thereof, oleic acid, stearic acid, palmitic acid, linoleic acid, salicylic acid, vinylcyclohexene and the like.

As the additional reducing agent, examples of the carbohydrate may include sugar, wheat flour, starch, monosaccharides such as glucose, dextrose and fructose, disaccharides such as sucrose, maltose and lactose, trisaccharides, tetrasaccharides, polysaccharides such as starch, cellulose, glycogen, pectin, agar, carrageenan, natural rubber and mixtures thereof. However, the additional reducing agent capable of being used in the present disclosure is not limited to the above examples.

In the present disclosure, the additional reducing agent preferably includes glycerin, ethylene glycol, ethanol and combinations thereof.

When using the additional reducing agent, with regard to the total reducing agent including both the additional reducing agent and the mixed reducing agent, the molar ratio of the total reducing agent/nitrogen dioxide is 0.5-5, and preferably 0.5-4. If the molar ratio of the total reducing agent/nitrogen dioxide in exhaust gas is less than 0.5, it is difficult to expect the effect of decreasing nitrogen dioxide content. On the other hand, a molar ratio thereof greater than 5 is undesirable from the viewpoints of reducing agent costs and side reactions.

Also, when using the additional reducing agent, the molar ratio of the additional reducing agent to the mixed reducing agent may be 1:1 to 1:4. Since the additional reducing agent is intended to assist the mixed reducing agent, use thereof in a larger amount than the mixed reducing agent is undesirable from the viewpoints of efficiency of decreasing nitrogen dioxide content and reducing agent costs.

The mixed reducing agent and the additional reducing agent may be injected into the WHB in a gas phase via a vaporizer, which is advantageous because dispersion is high compared to liquid injection. Moreover, an auxiliary injection fluid may be used to inject the mixed reducing agent and the additional reducing agent into the exhaust gas discharged from the catalyst regeneration reactor. The auxiliary injection fluid is intended to allow the reducing agent to be extensively injected into the exhaust gas, and an inert gas or liquid that is not reactive with the reducing agent may be used. In particular, when the reducing agent is injected in a liquid phase, a solvent having high solubility of the reducing agent may be used as the auxiliary injection fluid.

Also, the injection of the reducing agent into the exhaust gas is performed using the reducing agent alone or in combination with the auxiliary injection fluid, and the injection method is not particularly limited, so long as extensive injection of the reducing agent into the exhaust gas is possible. For example, the injection method may include the use of a nozzle, a reductant injection grid (RIG), etc.

The exhaust gas subjected to the reduction step of the present disclosure as described above is discharged into the atmosphere through a stack. Here, the nitrogen dioxide content in the exhaust gas that is discharged is less than 15 ppm, preferably 12 ppm or less, more preferably 10 ppm or less, and more preferably 9 ppm or less. By decreasing the nitrogen dioxide content in the exhaust gas to the above numerical values, it is possible to prevent the generation of a yellow plume, which is the aim of the present disclosure.

Turning again to FIG. 1, before the exhaust gas emitted from the WHB of the present disclosure is discharged through the stack, it may undergo heat exchange with the compressed air for a catalyst regeneration reaction in an air pre-heater (APH) to thus preheat the air. This helps to heat the air for catalyst regeneration, which is economically advantageous from the viewpoint of the olefin production process.

A better understanding of the present disclosure will be given through the following examples, which are merely set forth to illustrate the present disclosure but are not to be construed as limiting the scope of the present disclosure.

EXAMPLES

Test Example 1. Laboratory Test

Figure 2:
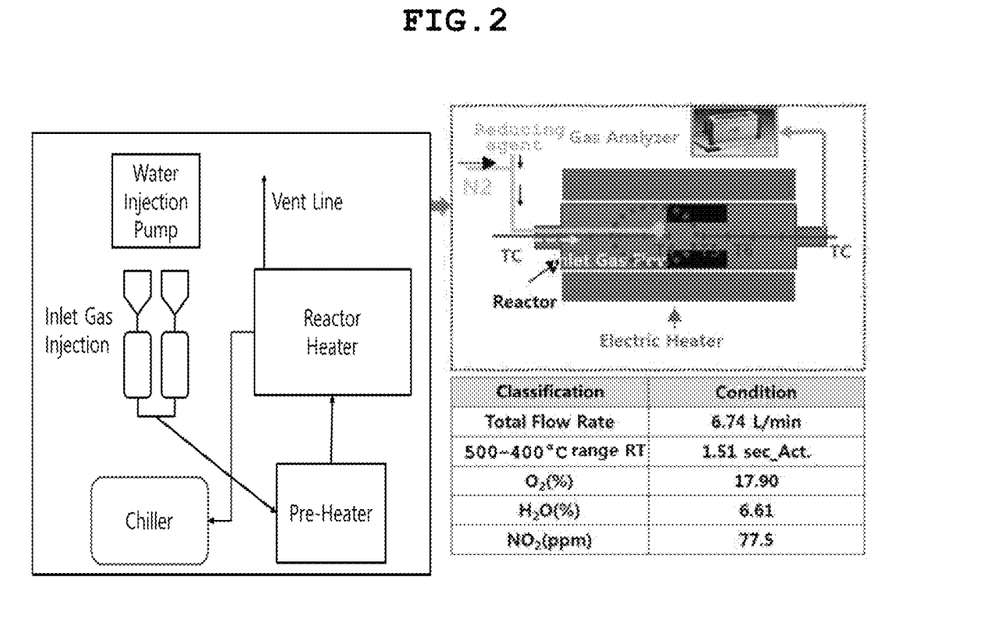
FIG. 2 shows a laboratory test unit and laboratory test conditions used in the performance test in Test Example 1 of the present disclosure.

When a process of decreasing nitrogen dioxide content in exhaust gas having a high temperature of 400 to 500° C. on a laboratory scale was performed in a WHB, the basic performance depending on the type of the reducing agent was tested. Ethanol (EtOH) and ethylene glycol (EG) were used as the reducing agent, and the test unit and test conditions were as shown in FIG. 2.

Air balance gas containing $NO_2$ at a specific concentration was preheated using a pre-heater and then injected into a reactor to thus adjust the temperature thereof using an electric heater so as to reach the test temperature. After the temperature of the gas reached the test temperature, the reducing agent was injected through a separate line upstream of the reactor. Thereafter, the gas discharged downstream of the reactor was analyzed using a gas analyzer.

Test Example 1-1. Performance Comparison of Single Reducing Agent

EtOH was used as a reducing agent, the temperature of the reactor was controlled to about 400° C., and then the reducing agent was injected at a molar ratio of reducing agent/nitrogen dioxide of 0.5, after which the composition of the exhaust gas at the outlet of the reactor was analyzed using a gas analyzer.

Also, the reducing agent was injected under the same conditions, with the exception that the molar ratio thereof was adjusted to each of 1.0, 1.5 and 2.0, after which the composition of the exhaust gas at the outlet of the reactor was analyzed using a gas analyzer.

In addition, the temperature of the reactor was changed to about 450° C. and about 500° C., and the reducing agent was injected at different molar ratios, as described above, after which the composition of the exhaust gas at the outlet of the reactor was analyzed.

Likewise, the EtOH reducing agent was replaced with EG, and the reducing agent was injected at different molar ratios of reducing agent/nitrogen dioxide into the reactor at different temperatures, as described above, after which the composition of the exhaust gas at the outlet of the reactor was analyzed.

Figure 3:
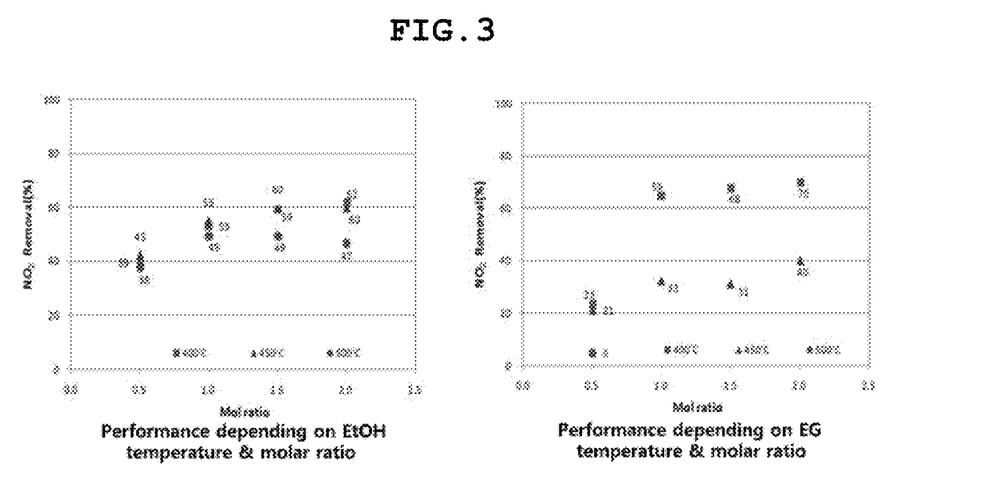
FIG. 3 shows the performance test results depending on the temperature and molar ratio of a single reducing agent, performed in Test Example 1-1 of the present disclosure.

The results of Test Example 1-1 are shown in FIG. 3 as graphs of the molar ratio versus the nitrogen dioxide removal rate.

As shown in FIG. 3, EtOH exhibited a nitrogen dioxide removal rate of 30-40% or more when it came into contact with exhaust gas at 450° C. or higher. On the other hand, EG exhibited a nitrogen dioxide removal rate of 60% or more when it came into contact with exhaust gas at 400° C., and showed a significant difference in the removal rate compared to when the reducing agent was injected at positions at which temperatures was 450° C. or higher. Therefore, it can be seen that EtOH is a reducing agent having advantageous performance at a temperature of 450° C. or higher and EG is a reducing agent having advantageous performance at a temperature of 450° C. or lower. Moreover, when using the reducing agent, it can be found that the temperature having optimum performance for each reducing agent is different.

Test Example 1-2. Performance Comparison of Mixed Reducing Agent

A mixed reducing agent (EtOH:EG=40:60) was prepared by mixing EtOH and EG such that the molar ratio of EtOH:EG was 40:60. The mixed reducing agent (EtOH:EG=40:60) was injected into exhaust gas at different reactor temperatures and different molar ratios of reducing agent/nitrogen dioxide, as in Test Example 1-1, after which the composition of the exhaust gas at the outlet of the reactor was analyzed.

In addition, a mixed reducing agent (EtOH:EG=60:40) was prepared by mixing EtOH and EG such that the molar ratio of EtOH:EG was 60:40. Thereafter, a mixed reducing agent (EtOH:EG=60:40) having a different composition was used in lieu of the mixed reducing agent (EtOH:EG=40:60), and was injected into exhaust gas at different injection positions and different molar ratios of reducing agent/nitrogen dioxide, as in the above test, after which the composition of the exhaust gas at the outlet of the reactor was analyzed.

Figure 4:
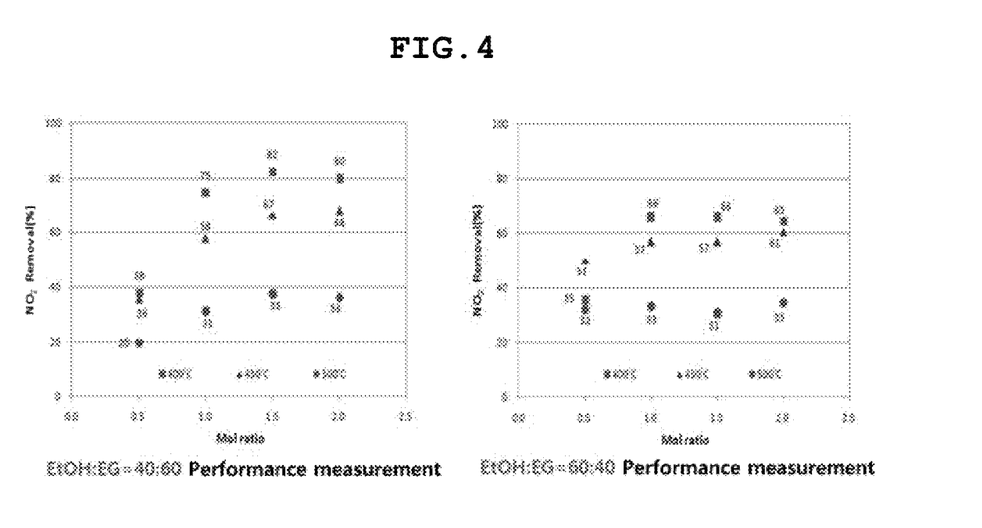
FIG. 4 shows the performance test results depending on the temperature and composition ratio of a mixed reducing agent, performed in Test Example 1-2 of the present disclosure.

The results of Test Example 1-2 are shown in FIG. 4 as graphs of the molar ratio versus the nitrogen dioxide removal rate.

As shown in FIG. 4, when the mixed reducing agent came into contact with exhaust gas at 400° C., the nitrogen dioxide removal rate was higher than when it came into contact with exhaust gas at 450° C. or higher. As with the use of the single mixing agent of Test Example 1-1, it can be found that a temperature resulting in optimum performance exists even when using the mixed reducing agent of EtOH and EG, and also that the temperature depends on the composition of the reducing agent.

Also, when comparing the nitrogen dioxide removal rates when using the mixed reducing agent (EtOH:EG=40:60) and the mixed reducing agent (EtOH:EG=60:40) in FIG. 4, the mixed reducing agent (EtOH:EG=40:60) exhibited a removal rate of 70% or more, thereby manifesting more advantageous nitrogen dioxide reduction performance.

Moreover, when comparing FIGS. 3 and 4, it can be found that the nitrogen dioxide removal rate was significantly increased when using the mixed reducing agent (EtOH:EG=40:60) compared to when using the single reducing agent of EtOH or EG.

Therefore, from the result of Test Example 1-2, it can be concluded that, when using the mixed reducing agent, the reduction performance can vary depending on the composition of the mixed reducing agent, and also that, by controlling the composition ratio of the mixed reducing agent, the development of a mixed reducing agent having reduction performance superior to that of a single reducing agent is possible.

Test Example 2. WHB On-Site Simulation Pilot Test

Figure 5:
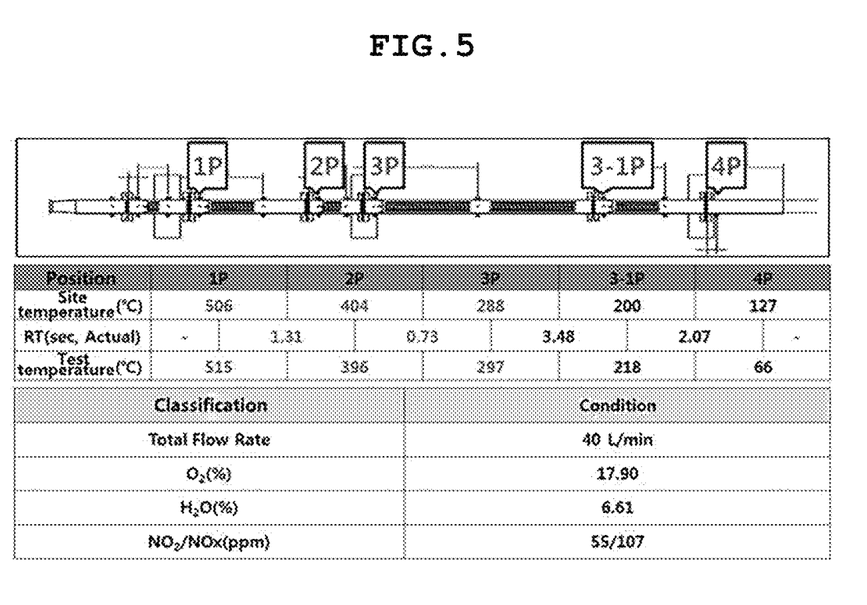
FIG. 5 shows the test conditions of the on-site simulation pilot test according to an embodiment of the present disclosure.
Figure 6:
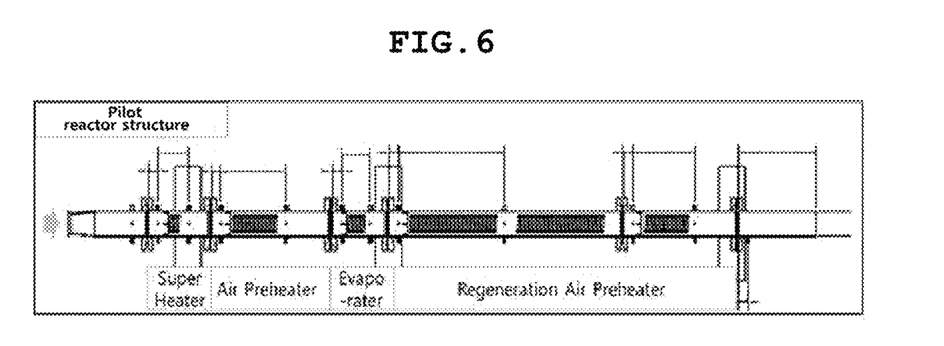
FIG. 6 shows the test unit of the on-site simulation pilot test performed in Test Example 2 of the present disclosure.

In order to evaluate the reducing agent and processing conditions suitable for exhaust gas containing nitrogen dioxide generated in the PDH process, a WHB simulation reactor having an exhaust gas temperature gradient of 100 to 500° C. on a pilot scale was installed, and a test was performed to measure the conversion rate of nitrogen dioxide in exhaust gas by varying the position of injection into the reactor, total injection molar ratio, injection method, and type of reducing agent. The specific test unit and test conditions are as shown in FIGS. 5 and 6 and in Tables 1 to 8 below.

Gas having a composition similar to the exhaust gas was controlled to a temperature of about 600° C. and introduced into the simulation reactor. As the results of Test Example 2, the composition of the exhaust gas at the outlet of the reactor and the nitrogen dioxide conversion rate under individual conditions are shown in Tables 1 to 8 below.

TABLE 1

| No. | Injected reducing agent 500° C. | Injected reducing agent 400° C. | Total injection molar ratio | Injection method | Injection position 500° C. | Injection position 400° C. | Measurement position | O$_2$ (%) | CO (ppm) | NO (ppm) | NO$_2$ (ppm) | NO$_x$ (ppm) | Conversion rate (%) |
|---|---|---|---|---|---|---|---|---|---|---|---|---|---|
| 1 |  | GL:EG(65:35) | 2.0 | Single |  | 2.0 | 4P | 18.52 | 16 | 98 | 19 | 117 | 65.5 |
| 2 | GL:EG(65:35) | GL:EG(65:35) | 3.0 | Double | 1.0 | 2.0 | 4P | 18.58 | 47 | 100 | 15 | 115 | 72.7 |
| 3 | EtOH (100%) | GL:EG(65:35) | 2.5 | Double | 0.5 | 2.0 | 4P | 18.35 | 20 | 99 | 16 | 115 | 70.9 |
| 4 | EtOH (100%) | GL:EG(65:35) | 3.5 | Double | 1.5 | 2.0 | 4P | 18.38 | 21 | 103 | 15 | 118 | 72.7 |
| 5 | EG (100%) | GL:EG(65:35) | 2.5 | Double | 0.5 | 2.0 | 4P | 18.49 | 23 | 103 | 15 | 118 | 72.7 |
| 6 | EG (100%) | GL:EG(65:35) | 3.5 | Double | 1.5 | 2.0 | 4P | 18.61 | 48 | 105 | 16 | 121 | 70.9 |
| 7 | EtOH:EG(40:60) | GL:EG(65:35) | 2.5 | Double | 0.5 | 2.0 | 4P | 18.62 | 25 | 102 | 16 | 118 | 70.9 |
| 8 | EtOH:EG(40:60) | GL:EG(65:35) | 3.5 | Double | 1.5 | 2.0 | 4P | 18.61 | 30 | 100 | 16 | 116 | 70.9 |

TABLE 2

| No. | Injected reducing agent 500° C. | Injected reducing agent 400° C. | Total injection molar ratio | Injection method | Injection position 500° C. | Injection position 400° C. | Measurement position | O$_2$ (%) | CO (ppm) | NO (ppm) | NO$_2$ (ppm) | NO$_x$ (ppm) | Conversion rate (%) |
|---|---|---|---|---|---|---|---|---|---|---|---|---|---|
| 9 |  |  |  | Double |  |  | 4P | 18.49 | 6 | 52 | 55 | 107 |  |
| 10 | GL:EG(65:35) | GL:EG(65:35) | 1.0 | Double | 0.5 | 0.5 | 4P | 18.55 | 30 | 83 | 30 | 113 | 45.5 |
| 11 | GL:EG(65:35) | GL:EG(65:35) | 1.5 | Double | 0.5 | 1.0 | 4P | 18.57 | 25 | 95 | 21 | 116 | 61.8 |
| 12 | GL:EG(65:35) | GL:EG(65:35) | 2.0 | Double | 0.5 | 1.5 | 4P | 18.62 | 26 | 98 | 18 | 116 | 67.3 |
| 13 | GL:EG(65:35) | GL:EG(65:35) | 2.5 | Double | 0.5 | 2.0 | 4P | 18.59 | 34 | 98 | 16 | 114 | 70.9 |
| 14 | GL:EG(65:35) | GL:EG(65:35) | 1.5 | Double | 1.0 | 0.5 | 4P | 18.58 | 40 | 92 | 22 | 114 | 60.0 |
| 15 | GL:EG(65:35) | GL:EG(65:35) | 2.0 | Double | 1.0 | 1.0 | 4P | 18.56 | 41 | 97 | 18 | 115 | 67.3 |
| 16 | GL:EG(65:35) | GL:EG(65:35) | 2.5 | Double | 1.0 | 1.5 | 4P | 18.56 | 42 | 99 | 16 | 115 | 70.9 |
| 17 | GL:EG(65:35) | GL:EG(65:35) | 3.0 | Double | 1.0 | 2.0 | 4P | 18.58 | 47 | 100 | 15 | 115 | 72.7 |

TABLE 3

| No. | Injected reducing agent 500° C. | Injected reducing agent 400° C. | Total injection molar ratio | Injection method | Injection position 500° C. | Injection position 400° C. | Measurement position | O$_2$ (%) | CO (ppm) | NO (ppm) | NO$_2$ (ppm) | NO$_x$ (ppm) | Conversion rate (%) |
|---|---|---|---|---|---|---|---|---|---|---|---|---|---|
| 18 |  |  |  |  |  |  | 4P | 18.45 | 6 | 52 | 55 | 107 |  |
| 19 | EtOH(100%) |  | 0.5 | Single | 0.5 |  | 4P | 18.42 | 8 | 55 | 52 | 107 | 5.5 |
| 20 | EtOH(100%) |  | 1.0 | Single | 1.0 |  | 4P | 18.46 | 10 | 58 | 50 | 108 | 9.1 |
| 21 | EtOH(100%) |  | 1.5 | Single | 1.5 |  | 4P | 18.42 | 11 | 59 | 49 | 108 | 10.9 |
| 22 | EtOH(100%) |  | 2.0 | Single | 2.0 |  | 4P | 18.47 | 12 | 60 | 49 | 109 | 10.9 |
| 23 | EtOH(100%) | GL:EG(65:35) | 1.0 | Double | 0.5 | 0.5 | 4P | 18.43 | 14 | 78 | 34 | 112 | 38.2 |
| 24 | EtOH(100%) | GL:EG(65:35) | 1.5 | Double | 0.5 | 1.0 | 4P | 18.44 | 17 | 93 | 24 | 117 | 56.4 |
| 25 | EtOH(100%) | GL:EG(65:35) | 2.0 | Double | 0.5 | 1.5 | 4P | 18.39 | 18 | 99 | 18 | 117 | 67.3 |
| 26 | EtOH(100%) | GL:EG(65:35) | 2.5 | Double | 0.5 | 2.0 | 4P | 18.35 | 20 | 99 | 16 | 115 | 70.9 |

TABLE 4

| No. | Injected reducing agent 500° C. | Injected reducing agent 400° C. | Total injection molar ratio | Injection method | Injection position 500° C. | Injection position 400° C. | Measurement position | O$_2$ (%) | CO (ppm) | NO (ppm) | NO$_2$ (ppm) | NO$_x$ (ppm) | Conversion rate (%) |
|---|---|---|---|---|---|---|---|---|---|---|---|---|---|
| 18 |  |  |  |  |  |  | 4P | 18.45 | 6 | 52 | 55 | 107 |  |
| 27 | EtOH(100%) | GL:EG(65:35) | 1.5 | Double | 1.0 | 0.5 | 4P | 18.36 | 15 | 81 | 32 | 113 | 41.8 |
| 28 | EtOH(100%) | GL:EG(65:35) | 2.0 | Double | 1.0 | 1.0 | 4P | 18.41 | 16 | 94 | 20 | 114 | 63.6 |
| 29 | EtOH(100%) | GL:EG(65:35) | 2.5 | Double | 1.0 | 1.5 | 4P | 18.32 | 20 | 99 | 17 | 116 | 69.1 |
| 30 | EtOH(100%) | GL:EG(65:35) | 3.0 | Double | 1.0 | 2.0 | 4P | 18.33 | 22 | 101 | 16 | 117 | 70.9 |
| 31 | EtOH(100%) | GL:EG(65:35) | 2.0 | Double | 1.5 | 0.5 | 4P | 18.35 | 16 | 83 | 31 | 114 | 43.6 |

TABLE 4-continued

| | Injected reducing agent | | Total injection molar ratio | Injection method | Injection position | | Measurement position | Measurement concentration | | | | | Conversion rate (%) |
|---|---|---|---|---|---|---|---|---|---|---|---|---|---|
| No. | 500° C. | 400° C. | | | 500° C. | 400° C. | | O₂ (%) | CO (ppm) | NO (ppm) | NO₂ (ppm) | NOₓ (ppm) | |
| 32 | EtOH(100%) | GL:EG(65:35) | 2.5 | Double | 1.5 | 1.0 | 4P | 18.35 | 19 | 98 | 20 | 118 | 63.6 |
| 33 | EtOH(100%) | GL:EG(65:35) | 3.0 | Double | 1.5 | 1.5 | 4P | 18.4 | 21 | 103 | 17 | 120 | 69.1 |
| 34 | EtOH(100%) | GL:EG(65:35) | 3.5 | Double | 1.5 | 2.0 | 4P | 18.38 | 21 | 103 | 15 | 118 | 72.7 |
| 35 | EtOH(100%) | GL:EG(65:35) | 2.5 | Double | 2.0 | 0.5 | 4P | 18.3 | 19 | 85 | 29 | 114 | 47.3 |
| 36 | EtOH(100%) | GL:EG(65:35) | 3.0 | Double | 2.0 | 1.0 | 4P | 18.3 | 20 | 96 | 20 | 116 | 63.6 |
| 37 | EtOH(100%) | GL:EG(65:35) | 3.5 | Double | 2.0 | 1.5 | 4P | 18.32 | 23 | 100 | 17 | 117 | 69.1 |
| 38 | EtOH(100%) | GL:EG(65:35) | 4.0 | Double | 2.0 | 2.0 | 4P | 18.31 | 29 | 100 | 17 | 117 | 69.1 |

TABLE 5

| | Injected reducing agent | | Total injection molar ratio | Injection method | Injection position | | Measurement position | Measurement concentration | | | | | Conversion rate (%) |
|---|---|---|---|---|---|---|---|---|---|---|---|---|---|
| No. | 500° C. | 400° C. | | | 500° C. | 400° C. | | O₂ (%) | CO (ppm) | NO (ppm) | NO₂ (ppm) | NOₓ (ppm) | |
| 39 | | | | | | | 4P | 18.47 | 6 | 52 | 55 | 107 | |
| 40 | EG (100%) | | 0.5 | Single | 0.5 | | 4P | 18.51 | 18 | 61 | 48 | 109 | 12.7 |
| 41 | EG (100%) | | 1.0 | Single | 1.0 | | 4P | 18.46 | 27 | 68 | 43 | 111 | 21.8 |
| 42 | EG (100%) | | 1.5 | Single | 1.5 | | 4P | 18.53 | 31 | 76 | 37 | 113 | 32.7 |
| 43 | EG (100%) | | 2.0 | Single | 2.0 | | 4P | 18.51 | 38 | 78 | 36 | 114 | 34.5 |
| 44 | EG (100%) | GL:EG (65:35) | 1.0 | Double | 0.5 | 0.5 | 4P | 18.53 | 20 | 87 | 30 | 117 | 45.5 |
| 45 | EG (100%) | GL:EG (65:35) | 1.5 | Double | 0.5 | 1.0 | 4P | 18.51 | 20 | 98 | 21 | 119 | 61.8 |
| 46 | EG (100%) | GL:EG (65:35) | 2.0 | Double | 0.5 | 1.5 | 4P | 18.49 | 26 | 101 | 18 | 119 | 67.3 |
| 47 | EG (100%) | GL:EG (65:35) | 2.5 | Double | 0.5 | 2.0 | 4P | 18.49 | 23 | 103 | 15 | 118 | 72.7 |

TABLE 6

| | Injected reducing agent | | Total injection molar ratio | Injection method | Injection position | | Measurement position | Measurement concentration | | | | | Conversion rate (%) |
|---|---|---|---|---|---|---|---|---|---|---|---|---|---|
| No. | 500° C. | 400° C. | | | 500° C. | 400° C. | | O₂ (%) | CO (ppm) | NO (ppm) | NO₂ (ppm) | NOₓ (ppm) | |
| 39 | | | | | | | 4P | 18.47 | 6 | 52 | 55 | 107 | |
| 48 | EG (100%) | GL:EG (65:35) | 1.5 | Double | 1 | 0.5 | 4P | 18.51 | 28 | 92 | 92 | 118 | 52.7 |
| 49 | EG (100%) | GL:EG (65:35) | 2.0 | Double | 1 | 1.0 | 4P | 18.47 | 29 | 101 | 101 | 119 | 67.3 |
| 50 | EG (100%) | GL:EG (65:35) | 2.5 | Double | 1 | 1.5 | 4P | 18.52 | 32 | 104 | 104 | 120 | 70.9 |
| 51 | EG (100%) | GL:EG (65:35) | 3.0 | Double | 1 | 2.0 | 4P | 18.45 | 38 | 103 | 103 | 118 | 72.7 |
| 52 | EG (100%) | GL:EG (65:35) | 2.0 | Double | 1.5 | 0.5 | 4P | 18.57 | 40 | 90 | 90 | 116 | 52.7 |
| 53 | EG (100%) | GL:EG (65:35) | 2.5 | Double | 1.5 | 1.0 | 4P | 18.53 | 44 | 99 | 99 | 119 | 63.6 |
| 54 | EG (100%) | GL:EG (65:35) | 3.0 | Double | 1.5 | 1.5 | 4P | 18.59 | 47 | 101 | 101 | 118 | 69.1 |
| 55 | EG (100%) | GL:EG (65:35) | 3.5 | Double | 1.5 | 2.0 | 4P | 18.61 | 48 | 105 | 105 | 121 | 70.9 |

TABLE 7

| | Injected reducing agent | | Total injection molar ratio | Injection method | Injection position | | Measurement position | Measurement concentration | | | | | Conversion rate (%) |
|---|---|---|---|---|---|---|---|---|---|---|---|---|---|
| No. | 500° C. | 400° C. | | | 500° C. | 400° C. | | O₂ (%) | CO (ppm) | NO (ppm) | NO₂ (ppm) | NOₓ (ppm) | |
| 56 | | | | | | | 4P | 18.61 | 6 | 52 | 55 | 107 | |
| 57 | EtOH:EG(40:60) | | 0.5 | Single | 0.5 | | 4P | 18.61 | 12 | 60 | 50 | 110 | 9.1 |
| 58 | EtOH:EG(40:60) | | 1.0 | Single | 1.0 | | 4P | 18.59 | 19 | 63 | 48 | 111 | 12.7 |
| 59 | EtOH:EG(40:60) | | 1.5 | Single | 1.5 | | 4P | 18.58 | 24 | 69 | 43 | 112 | 21.8 |
| 60 | EtOH:EG(40:60) | | 2.0 | Single | 2.0 | | 4P | 18.57 | 27 | 72 | 41 | 113 | 25.5 |
| 61 | EtOH:EG(40:60) | GL:EG (65:35) | 0.5 | Double | 0.5 | 0.5 | 4P | 18.61 | 18 | 83 | 33 | 116 | 40.0 |
| 62 | EtOH:EG(40:60) | GL:EG (65:35) | 1.0 | Double | 0.5 | 1.0 | 4P | 18.61 | 21 | 95 | 22 | 117 | 60.0 |

TABLE 7-continued

| No. | Injected reducing agent 500° C. | 400° C. | Total injection molar ratio | Injection method | Injection position 500° C. | 400° C. | Measurement position | $O_2$ (%) | CO (ppm) | NO (ppm) | $NO_2$ (ppm) | $NO_x$ (ppm) | Conversion rate (%) |
|---|---|---|---|---|---|---|---|---|---|---|---|---|---|
| 63 | EtOH:EG(40:60) | GL:EG(65:35) | 1.5 | Double | 0.5 | 1.5 | 4P | 18.63 | 25 | 95 | 18 | 113 | 67.3 |
| 64 | EtOH:EG(40:60) | GL:EG(65:35) | 2.0 | Double | 0.5 | 2.0 | 4P | 18.62 | 25 | 102 | 16 | 118 | 70.9 |

TABLE 8

| No. | Injected reducing agent 500° C. | 400° C. | Total injection molar ratio | Injection method | Injection position 500° C. | 400° C. | Measurement position | $O_2$ (%) | CO (ppm) | NO (ppm) | $NO_2$ (ppm) | $NO_x$ (ppm) | Conversion rate (%) |
|---|---|---|---|---|---|---|---|---|---|---|---|---|---|
| 56 | | | | | | | 4P | 18.61 | 6 | 52 | 55 | 107 | |
| 65 | EtOH:EG(40:60) | GL:EG(65:35) | 1.5 | Double | 1.0 | 0.5 | 4P | 18.58 | 23 | 83 | 31 | 114 | 43.6 |
| 66 | EtOH:EG(40:60) | GL:EG(65:35) | 2.0 | Double | 1.0 | 1.0 | 4P | 18.54 | 31 | 93 | 22 | 115 | 60.0 |
| 67 | EtOH:EG(40:60) | GL:EG(65:35) | 2.5 | Double | 1.0 | 1.5 | 4P | 18.61 | 28 | 97 | 19 | 116 | 65.5 |
| 68 | EtOH:EG(40:60) | GL:EG(65:35) | 3.0 | Double | 1.0 | 2.0 | 4P | 18.63 | 32 | 99 | 17 | 116 | 69.1 |
| 69 | EtOH:EG(40:60) | GL:EG(65:35) | 2.0 | Double | 1.5 | 0.5 | 4P | 18.63 | 28 | 87 | 27 | 114 | 50.9 |
| 70 | EtOH:EG(40:60) | GL:EG(65:35) | 2.5 | Double | 1.5 | 1.0 | 4P | 18.59 | 29 | 94 | 20 | 114 | 63.6 |
| 71 | EtOH:EG(40:60) | GL:EG(65:35) | 3.0 | Double | 1.5 | 1.5 | 4P | 18.58 | 32 | 98 | 17 | 115 | 69.1 |
| 72 | EtOH:EG(40:60) | GL:EG(65:35) | 3.5 | Double | 1.5 | 2.0 | 4P | 18.61 | 30 | 100 | 16 | 116 | 70.9 |

As is apparent from the above results, in the removal of nitrogen dioxide in exhaust gas generated in the catalyst regeneration step in the PDH process, it can be found that the use of the mixed reducing agent of glycerin (GL) and ethylene glycol (EG) is preferable. For example, when comparing Test Examples 2-1, 2-19 to 22, 2-40 to 43, and 2-57 to 2-60 in Tables 1 to 8, the use of each of EtOH, EG and EtOH:EG (40:60) as the reducing agent exhibited a conversion rate of nitrogen dioxide in exhaust gas of less than 35%, whereas the use of GL:EG (65:35) as the reducing agent exhibited a conversion rate of 65% or more, which is a significant difference.

Also, as is apparent from the above results, it can be found that injecting an additional reducing agent along with the mixed reducing agent is more effective at removing nitrogen dioxide from exhaust gas. For example, with reference to Table 1 and FIG. 5, in Test Examples 2-2 to 2-8, GL:EG, EtOH, EG, and EtOH:EG were injected as the additional reducing agent to 1P, located upstream of 2P, at which the mixed reducing agent was injected, and when comparing the nitrogen dioxide conversion rate thereof with the conversion rate of Test Example 2-1, it appears that the conversion rate is increased by 5% or more when the additional reducing agent is injected.

Meanwhile, the gas used in Test Example 2 has a total $NO_x$ concentration of about 107 ppm or more and a $NO_2$ concentration of about 55 ppm, and thus it should be noted that the test was conducted under conditions that are more severe than the total $NO_x$ and $NO_2$ concentrations in exhaust gas discharged during actual processing. When the method of removing nitrogen dioxide according to the present disclosure is applied to exhaust gas during actual processing, yellow plumes can be prevented from occurring, as is apparent from Examples 1 to 7 below.

Examples 1 to 7. On-Site Process in PDH Plant

Figure 7:
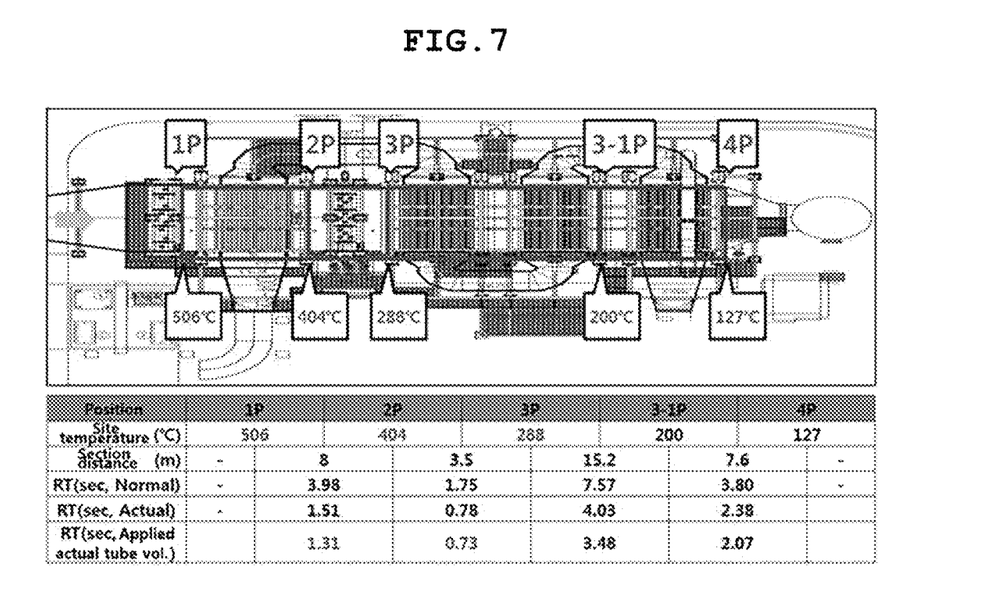
FIG. 7 shows the on-site unit and the on-site unit conditions according to an embodiment of the present disclosure.

In the WHB of an actual plant running the PDH process, a reducing agent, particularly a mixed reducing agent GL:EG (65:35), was injected through RIG to the position of the WHB at which the temperature of exhaust gas flowing therein was about 400 to 420° C. The structure of the on-site WHB is as shown in FIG. 7.

In the PDH plant operating continuously, the process of decreasing nitrogen dioxide content is also continuously performed, and the concentration of nitrogen dioxide discharged through a stack in Examples 1 to 7 was measured on site for one week at 1-day (24-hr) intervals. The processing conditions of Examples 1 to 7 and the results thereof are shown as daily average values in Table 9 below.

TABLE 9

| Example | 1 | 2 | 3 | 4 | 5 | 6 | 7 |
|---|---|---|---|---|---|---|---|
| Reducing agent injection temperature (° C.) | 409.57 | 408.69 | 408.55 | 408.22 | 408.26 | 409.32 | 409.44 |
| Reducing agent composition (GL:EG, molar ratio) | 65:35 | 65:35 | 65:35 | 65:35 | 65:35 | 65:35 | 65:35 |
| Reducing agent injection flow rate (kg/h) | 185.38 | 177.89 | 185.18 | 169.13 | 165.13 | 153.87 | 165.57 |
| $NO_2$ before reaction (ppm) | 47.63 | 47.05 | 46.41 | 44.47 | 45.18 | 44.12 | 45.44 |
| Stack Out   $NO_2$(ppm) | 10.37 | 9.68 | 8.53 | 8.30 | 8.40 | 8.62 | 8.05 |
| Composition   $O_2$(mol %) | 17.70 | 17.73 | 17.77 | 17.93 | 18.03 | 18.08 | 18.03 |
| Conversion rate(%) | 78.23 | 79.43 | 81.62 | 81.34 | 81.41 | 80.46 | 82.28 |

As is apparent from Table 9, it can be found that the removal of nitrogen dioxide in exhaust gas generated during actual operation of a PDH plant can be easily achieved by bringing the mixed reducing agent GL:EG (65:35) into contact with exhaust gas at about 400 to about 420° C. Therefore, it can be concluded that the nitrogen dioxide content in exhaust gas discharged into the atmosphere through the stack is less than about 11 ppm, making it possible to effectively prevent the generation of yellow plumes in the PDH plant.

Although preferred embodiments of the present disclosure have been described as above, the present disclosure is not limited to the specific embodiments described above, and various modifications can be carried out by those skilled in the art to which the disclosure pertains without departing from the gist of the present disclosure claimed in the claims, and these modifications should not be understood individually from the technical idea or prospect of the present disclosure.

The invention claimed is:

1. A method of decreasing a nitrogen dioxide content in exhaust gas generated during an olefin production process using selective non-catalytic reduction, comprising:
   (a) providing exhaust gas containing nitrogen dioxide generated in an olefin production process, wherein an oxygen content in the exhaust gas that is provided is 17 to 20 mol %, and a temperature of the exhaust gas that is provided is 500 to 600° C.;
   (b) reducing nitrogen dioxide by injecting a mixed reducing agent to the exhaust gas, the mixed reducing agent comprising glycerin and ethylene glycol, wherein step (b) is performed in a waste heat boiler (WHB), the mixed reducing agent is injected at a position of the waste heat boiler at which the temperature of the exhaust gas is 350 to 450° C., and a molar ratio of glycerin to ethylene glycol in the mixed reducing agent is 55-80:20-45; and
   (c) discharging the exhaust gas subjected to step (b) into an atmosphere,
   wherein step (b) comprises injecting an additional reducing agent to the exhaust gas at a position of the waste heat boiler at which the temperature of the exhaust gas is 550° C. or less but exceeds 450° C.

2. The method of claim 1, wherein a nitrogen dioxide content in the exhaust gas that is provided is 20 ppm or more.

3. The method of claim 1, wherein a hydrocarbon content in the exhaust gas that is provided is 50 to 2000 ppmv.

4. The method of claim 1, wherein the mixed reducing agent is injected such that a molar ratio of mixed reducing agent/nitrogen dioxide is 0.5-4.

5. The method of claim 1, wherein a nitrogen dioxide content in the exhaust gas that is discharged in step (c) is 12 ppm or less.

* * * * *